US008859480B2

(12) United States Patent
Lant et al.

(10) Patent No.: US 8,859,480 B2
(45) Date of Patent: Oct. 14, 2014

(54) DETERGENT COMPOSITIONS

(75) Inventors: Neil Joseph Lant, Newcastle upon Tyne (GB); Steven George Patterson, Tyne and Wear (GB)

(73) Assignee: The Procter & Gamble Company, Cincinnati, OH (US)

( * ) Notice: Subject to any disclaimer, the term of this patent is extended or adjusted under 35 U.S.C. 154(b) by 434 days.

(21) Appl. No.: 12/406,496

(22) Filed: Mar. 18, 2009

(65) Prior Publication Data

US 2009/0192066 A1 Jul. 30, 2009

Related U.S. Application Data

(63) Continuation of application No. 11/358,557, filed on Feb. 21, 2006, now abandoned.

(30) Foreign Application Priority Data

Feb. 22, 2005 (EP) .................................... 05250998

(51) Int. Cl.

| | |
|---|---|
| ***C12N 9/20*** | (2006.01) |
| ***C07H 21/04*** | (2006.01) |
| ***C11D 17/00*** | (2006.01) |
| ***C11D 3/06*** | (2006.01) |
| ***C11D 3/386*** | (2006.01) |
| ***C11D 3/12*** | (2006.01) |

(52) U.S. Cl.

CPC .............. *C11D 3/38627* (2013.01); *C11D 3/06* (2013.01); *C11D 3/128* (2013.01)

USPC ........... 510/294; 510/114; 510/296; 510/300; 510/392; 510/439; 510/441; 435/198; 435/252.3; 435/252.33; 435/252.8; 435/263; 435/320.1

(58) Field of Classification Search

USPC ........... 435/198, 252.3, 320.1, 252.33, 252.8, 435/263; 510/392, 114, 294, 296, 300, 439, 510/441

See application file for complete search history.

(56) References Cited

U.S. PATENT DOCUMENTS

| | | | | |
|---|---|---|---|---|
| 3,886,098 | A | 5/1975 | DiSalvo et al. | |
| 4,487,710 | A | 12/1984 | Kaminsky | |
| 5,663,136 | A | 9/1997 | Van Dijk et al. | |
| 5,869,438 | A * | 2/1999 | Svendsen et al. | 510/226 |
| 6,080,711 | A | 6/2000 | Brouwer et al. | |
| 6,232,285 | B1 | 5/2001 | Casteel et al. | |
| 6,939,702 | B1 * | 9/2005 | Vind et al. | 435/198 |
| 2002/0187910 | A1 * | 12/2002 | Speed et al. | 510/295 |

FOREIGN PATENT DOCUMENTS

| | | |
|---|---|---|
| GB | 1408969 | 10/1975 |
| GB | 1408970 | 10/1975 |
| JP | 2003-520021 A | 10/2004 |
| WO | WO 00/60063 A1 | 10/2000 |
| WO | WO-03097780 | 11/2003 |

OTHER PUBLICATIONS

Characteristics of Metalworking Fluids—The importance of pH and Reserve Alkalinity, TRIM Technical Bulletin, Master Chemical Corporation, 2006.*

PCT International Search Report, 4 Pages, Mailed Jul. 5, 2006.

* cited by examiner

*Primary Examiner* — Gregory R Delcotto
*Assistant Examiner* — Preeti Kumar
(74) *Attorney, Agent, or Firm* — Melissa G Krasovec

(57) ABSTRACT

Detergent compositions containing high efficiency lipase enzymes and specific detergent formulations comprising less than 10 wt % zeolite and phosphate builder are described. Preferred formulations comprise surfactants selected from alkyl benzene sulphonates in combination with alky ethoxylated sulfates or MES or non-ionic surfactants.

20 Claims, No Drawings

DETERGENT COMPOSITIONS

CROSS REFERENCE TO RELATED APPLICATIONS

This application is a Continuation of U.S. application Ser. No. 11/358,557 filed Feb. 21, 2006 now abandoned, and co-pending foreign Utility application Ser. No. 05 250 998.1 filed on Feb. 22, 2005.

TECHNICAL FIELD

The present invention relates to laundry detergent compositions and in particular to detergents comprising lipolytic or lipase enzymes.

BACKGROUND OF THE INVENTION AND PRIOR ART

Improved removal of greasy soils is a constant aim for laundry detergent manufacturers. In spite of the use of many effective surfactants and combinations of surfactants, especially when used at low water temperatures, many surfactant-based products still do not achieve complete removal of greasy/oily soils. Lipase enzymes have been used in detergents since the late 1980s for removal of fatty soils by breakdown of fatty soils into tri-glycerides.

Until relatively recently, the main commercially available lipase enzymes, such as Lipolase (trade name, Novozymes) worked particularly effectively at the lower moisture levels of the drying phase of the wash process. These enzymes tended to produce significant cleaning only in the second wash step because the active site of the enzyme was occupied by water during the washing process, so that fat breakdown was significant only on soils remaining on laundered clothes during the drying stage, the broken down fats then being removed in the next washing step. However, more recently, higher efficiency lipases have been developed that also work effectively during the wash phase of the cleaning process, so that as well as cleaning in the second washing step, a significant improvement in cleaning effect due to lipase enzyme can be found in the first wash-cycle. Examples of such enzymes are as described in WO0/60063 and Research Disclosure IP6553D. Such enzymes are referred to below as first wash lipases. Examples of such enzymes include certain variants of lipolase (wild-type *Humicola lanuginosa*) which should comprise one or more substitutions with positive amino acids near the N-terminal in the three-dimensional structure. The variants should further comprise a peptide addition at the C-terminal and/or should meet certain limitations on electrically charged amino acids at positions 90-101 and 210.

The problem facing the present inventors was how to maximise performance from this new generation of enzymes. The present inventors found that whilst a small benefit could be achieved formulating such enzymes according to present day detergent formulations by simply replacing existing lipase enzymes with the new generation of enzymes, a considerable improvement in performance was found by formulating the detergent compositions in a different way and even reducing the levels of some conventional detergent ingredients.

DEFINITION OF THE INVENTION

In accordance with the present invention there is provided a detergent composition comprising a lipase which is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15 Å° of E1 or Q249 with a positively charged amino acid; and (c) comprises a peptide addition at the C-terminal; and/or (d) comprises a peptide addition at the N-terminal and/or (e) meets the following limitations: i) comprises a negative amino acid in position E210 of said wild-type lipase; ii) comprises a negatively charged amino acid in the region corresponding to positions 90-101 of said wild-type lipase; and iii) comprises a neutral or negative amino acid at a position corresponding to N94 of said wild-type lipase and/or has a negative or neutral net electric charge in the region corresponding to positions 90-101 of said wild-type lipase; the detergent composition comprising less than 10 wt % aluminosilicate (anhydrous basis) and less than 10 wt % phosphate builder, the composition having a reserve alkalinity of greater than 4.

In accordance with the present invention there is provided a detergent composition comprising a lipase enzyme producing First Wash lard removal performance better than that produced by WT Lipolase (tradename from Novozymes) using the Lard First Wash Test described below, and the detergent composition comprising less than 10 wt % aluminosilicate builder and less than 10 wt % phosphate builder, the composition having a reserve alkalinity greater than 4. WT Lipolase from Novozymes is described in U.S. Pat. No. 5,869, 438, seq#2.

In a preferred aspect of the invention, the detergent compositions of the invention comprise less than 10 wt % builders selected from aluminosilicate (zeolite) builder and/or phosphate builder. In a further preferred aspect of the invention, the compositions comprise less than 8 wt % zeolite, or even less than 4 wt % and less than 8 wt % phosphate builder or even less than 4 wt %.

The present inventors have found that when a first wash lipase is used in conjunction with a low level of phosphate and zeolite builder, dramatically improved grease removal benefits are obtained compared to formulating lipase with conventional builder levels. Without wishing to be bound by theory, it is believed that this is driven by the presence of divalent cations enhancing lipase activity by (i) increasing the deposition of enzyme onto the fabric surface and/or (ii) enhancing the precipitation of insoluble fatty acid salts arising from the lipolysis enzymatic process.

While builder reduction or elimination might be expected to raise significant stain removal negatives on, for example, particulate and beverage stains, we have found that the compositions show unexpectedly good performance. Without wishing to be bound by theory it is believed that this is due to fatty acids released by the lipase during lipolysis of fatty soils acting to (i) destabilize these stains via a hardness sequestration effect and (ii) reduce the wash pH slightly resulting in lightening of pH-sensitive stains.

DETAILED DESCRIPTION OF THE INVENTION

Lipase Enzyme

The reference lipase used in this invention is the wild type lipase derived from *Humicola lanuginosa* strain DSM 4109. It is described in EP258068 and EP305216 and has the amino acid sequence shown in positions 1-269 of SEQ ID NO: 2 of U.S. Pat. No. 5,869,438. In this specification, the reference lipase is also referred to as Lipolase.

Substitution with Positive Amino Acid

The lipase of the invention comprises one or more (e.g. 2-4, particularly two) substitutions of an electrically neutral or negatively charged amino acid near E1 or Q249 with a positively charged amino acid, preferably R.

The substitution is at the surface of the three-dimensional structure within 15 Å of E1 or Q249, e.g. at any of positions 1-11, 90, 95, 169, 171-175, 192-211, 213-226, 228-258, 260-262.

The substitution may be within 10 Å of E1 or Q249, e.g. at any of positions 1-7, 10, 175, 195, 197-202, 204-206, 209, 215, 219-224, 230-239, 242-254.

The substitution may be within 15 Å of E1, e.g. at any of positions 1-11, 169, 171, 192-199, 217-225, 228-240, 243-247, 249, 261-262.

The substitution is most preferably within 10 Å of E1, e.g. at any of positions 1-7, 10, 219-224 and 230-239.

Thus, some preferred substitutions are S3R, S224R, P229R, T231R, N233R, D234R and T244R.

Peptide Addition at C-Terminal

The lipase may comprise a peptide addition attached to C-terminal L269. The peptide addition improves the first-wash performance in a variety of detergents.

The peptide addition preferably consists of 1-5 amino acids, e.g. 2, 3 or 4 amino acids. The amino acids of the peptide addition will be numbered 270, 271, etc.

The peptide addition may consist of electrically neutral (e.g. hydrophobic) amino acids, e.g. PGL or PG. In an alternative embodiment, the lipase peptide addition consists of neutral (e.g. hydrophobic) amino acids and the amino acid C, and the lipase comprises substitution of an amino acid with C at a suitable location so as to form a disulfide bridge with the C of the peptide addition. Examples are:

270C linked to G23C or T37C 271C linked to K24C, T37C, N26C or R81C 272C linked to D27C, T35C, E56C, T64C or R81C.

Amino Acids at Positions 90-101 and 210

The lipase used in the invention preferably meets certain limitations on electrically charged amino acids at positions 90-101 and 210. Thus, amino acid 210 may be negative. E210 may be unchanged or it may have the substitution E210D/C/Y, particularly E210D.

The lipase may comprise a negatively charged amino acid at any of positions 90-101 (particularly 94-101), e.g. at position D96 and/or E99.

Further, the lipase may comprise a neutral or negative amino acid at position N94, i.e. N94 (neutral or negative), e.g. N94N/D/E.

Also, the lipase may have a negative or neutral net electric charge in the region 90-101 (particularly 94-101), i.e. the number of negative amino acids is equal to or greater than the number of positive amino acids. Thus, the region may be unchanged from Lipolase, having two negative amino acids (D96 and E99) and one positive (K98), and having a neutral amino acid at position 94 (N94), or the region may be modified by one or more substitutions.

Alternatively, two of the three amino acids N94, N96 and E99 may have a negative or unchanged electric charge. Thus, all three amino acids may be unchanged or may be changed by a conservative or negative substitution, i.e. N94 (neutral or negative), D(negative) and E99(negative). Examples are N94D/E and D96E. Also, one of the three may be substituted so as to increase the electric charge, i.e. N94 (positive), D96 (neutral or positive) or E99 (neutral or positive). Examples are N94K/R, D96I/L/N/S/W or E99N/Q/K/R/H.

As discussed in WO00/60063, the substitution of a neutral with a negative amino acid (N94D/E), may improve the performance in an anionic detergent. The substitution of a neutral amino acid with a positive amino acid (N94K/R) may provide a variant lipase with good performance both in an anionic detergent and in an anionic/non-ionic detergent (a detergent with e.g. 40-70% anionic out of total surfactant). A substitution Q249R/K/H and/or a substitution of R209 with a neutral or negative amino acid (e.g. R209P/S) may be useful. The lipase may optionally comprise the substitution G91A.

The lipase may optionally comprise substitutions of one or more additional amino acids. Such substitutions may, e.g. be made according to principles known in the art, e.g. substitutions described in WO92/05249, WO94/25577, WO95/22615, WO97/04079 and WO97/07202. Specific examples of suitable combinations of substitutions are given in the table bridging pages 4 and 5 of WO00/60063. Nomenclature for amino acid modifications is as described in WO00/60063.

The preferred lipase enzymes are described in WO00/60063, the most preferred being Lipex (registered tradename of Novozymes), a variant of the *Humicola lanuginosa* (*Thermomyces lanuginosus*) lipase (Lipolase registered tradename of Novozymes) with the mutations T231R and N233R.

The lipase enzyme incorporated into the detergent compositions of the present invention is generally present in an amount of 10 to 20000 LU/g of the detergent composition, or even 100 to 10000 LU/g. The LU unit for lipase activity is defined in WO99/42566. The lipase dosage in the wash solution is typically from 0.01 to 5 mg/l active lipase protein, more typically from 0.1 to 2mg/l as enzyme protein. As a percentage by weight of the enzyme protein in the detergent composition, this is generally from 0.00001 to 2 wt %, more usually 0.0001 to 1% or even 0.001 to 0.5%.

The lipase enzyme may be incorporated into the detergent composition in any convenient form, generally in the form of a non-dusting granulate, a stabilised liquid or a protected, for example, coated enzyme particle.

Lard First Wash Test

Whether any specific lipase enzyme gives better First Wash lard removal performance than WT Lipolase (from Novozymes, described in U.S. Pat. No. 5,869,438, seq#2), can be determined by comparing the performance results of WT Lipolase with the performance results of the specific lipase enzyme according to the following test:

The wash performance of lipolytic enzymes is tested in a one cycle wash trial carried out in a thermostated Terg-O-Tometer (TOM) followed by line-drying. The experimental conditions are as follows:

Wash liquor: 1000 ml per beaker

Swatches: 7 flat cotton swatches (9×9 cm) (supplied by Warwick-Equest) per beaker Stain: Lard coloured red with sudan red dye (Sigma) (0.75 mg sudan red/g lard). 50 μl of lard/sudan red heated to 70° C. are applied to the centre of each swatch. After application of the stain the swatches are heated in an oven for 25 minutes at 75° C. and then stored overnight at room temperature.

Water for preparing wash liquor: 3.2 mM $Ca^{2+}/Mg^{2+}$ (in a ratio of 5:1)

Detergent: 5 g/l of detergent composition A.

Detergent Composition A:

0.300 g/l alkyl sulphate (AS; $C_{14-16}$)

0.650 g/l of alcohol ethoxylate (AEO; $C_{12-14}$, 6EO)

1.750 g/l zeolite P 0.145 g/l $Na_2CO_3$ 0.020 g/l Sokalan CP5 (BASF)

0.050g/l CMC(carboxy methyl cellulose)

5 g/l of detergent composition A are mixed into deionised water with added hardness (3.2 mM $Ca^{2+}/Mg^{2+}$ (5:1)) and the pH artificially adjusted to pH 10.2 by adding NaOH.

Lipase enzyme is added.

Concentration of lipolytic enzyme: 0 and 12500 LU/l

Wash time: 20 minutes

Wash temperature: 30° C.

Rinse: 15 minutes in running tap water

Drying: overnight at room conditions (approx. 20° C., 30-40% RH).

Evaluation: the reflectance was measured at 460 nm.

The percentage of lard removed is determined as:

Delta reflectance (dR) defined as:

(R(Swatches washed in detergent with lipase)-R(Swatches washed in detergent without lipase)

The reflectance (which may also be termed remission) is measured on an Elrepho 2000 apparatus from Datacolor which illuminates the sample with 2 xenon blitz lamps and measures the amount of reflected light so that entirely white corresponds to a 100% reflectance and entirely black a 0% reflectance. Comparing the results for lard removal due to the presence of enzyme, lipase enzymes giving better performance than WT Lipolase™ are suitable for use in the compositions of the present invention.

Builders

Commercially available laundry detergents comprise strong inorganic builder, with either phosphate builder typically sodium tripolyphosphate (STPP), or zeolite typically sodium aluminosilicate builder, being used as the predominant strong builder. Generally such strong builders are present at relatively high levels such as 15 to 20 wt % or even higher, for example even up to 40 wt %. In accordance with the present invention, the amount of strong builder selected from phosphate and/or zeolite builder is no greater than 10 wt % based on the total weight of the detergent composition, preferably below 8 wt %, or even below 5 or 4 or 3 or 2 or 1 wt %.

Thus, the compositions of the invention may comprise from 0 wt % to 10 wt % zeolite builder, and 0 wt % to 10 wt % phosphate builder, the total amount of phosphate and/or zeolite not exceeding 10 wt %, and preferably being below 10 wt % as described above. Preferably the compositions of the invention comprise from 0 wt % to 8 wt %, or from 0 wt % to 5 or 4 wt %, or from 0 wt % to 3 or even less than 2 wt % zeolite builder. It may even be preferred for the composition to be essentially free from zeolite builder. By essentially free from zeolite builder it is typically meant that the composition comprises no deliberately added zeolite builder. This is especially preferred if it is desirable for the composition to be very highly soluble, to minimise the amount of water-insoluble residues (for example, which may deposit on fabric surfaces), and also when it is highly desirable to have transparent wash liquor. Zeolite builders include zeolite A, zeolite X, zeolite P and zeolite MAP.

The compositions of the invention may comprise from 0 wt % to 10 wt % phosphate builder. The composition preferably comprises from 0 wt % to 8 wt %, or from 0 wt % to 5 or 4 wt %, or from 0 wt % to 3 or even 2 wt % phosphate builder. It may even be preferred for the composition to be essentially free from phosphate builder. By essentially free from phosphate builder it is typically meant that the composition comprises no deliberately added phosphate builder. This is especially preferred if it is desirable for the composition to have a very good environmental profile. Phosphate builders include sodium tripolyphosphate.

In a further preferred aspect of the invention, the total level of weak builders selected from layered silicate (SKS-6), citric acid, citrate salts and nitrilo triacetic acid or salt thereof is below 15 wt %, more preferably below 8 wt %, more preferably below 4 wt % or even below 3 or 2 wt % based on the total weight of the detergent composition. Typically the level of each of layered silicate, citric acid, citrate salts and nitrilo triacetic acid or salt thereof will be below 10 wt % or even below 5 wt % or wt % based on the total weight of the composition.

Although builders bring several benefits to the formulator, their main role is to sequester divalent metal ions (such as calcium and magnesium ions) from the wash solution that would otherwise interact negatively with the surfactant system. Builders are also effective at removing metal ions and inorganic soils from the fabric surface too, leading to improved removal of particulate and beverage stains. It would therefore be expected that reduction of their levels would negatively impact on cleaning performance and therefore, preparation of detergent compositions that are effective with the claimed reduced levels of phosphate and zeolite builders is surprising.

Reserve Alkalinity

As used herein, the term "reserve alkalinity" is a measure of the buffering capacity of the detergent composition (g/NaOH/100 g detergent composition) determined by titrating a 1% (w/v) solution of detergent composition with hydrochloric acid to pH 7.5 i.e in order to calculate Reserve Alkalinity as defined herein:

$$\text{Reserve Alkalinity (to pH 7.5) as \% alkali in g NaOH/100 g product} = \frac{T \times M \times 40 \times Vol}{10 \times \text{Wt} \times Aliquot}$$

$$\begin{aligned} T &= \text{titre (ml) to pH 7.5} \\ M &= \text{Molarity of HCl} = 0.2 \\ 40 &= \text{Molecular weight of NaOH} \\ Vol &= \text{Total volume (ie. 1000 ml)} \\ \text{Wt} &= \text{Weight of product (10 g)} \\ Aliquot &= \text{(100 ml)} \end{aligned}$$

Obtain a 10 g sample accurately weighed to two decimal places, of fully formulated detergent composition. The sample should be obtained using a Pascall sampler in a dust cabinet. Add the 10 g sample to a plastic beaker and add 200 ml of carbon dioxide-free deionised water. Agitate using a magnetic stirrer on a stirring plate at 150 rpm until fully dissolved and for at least 15 minutes. Transfer the contents of the beaker to a 1 litre volumetric flask and make up to 1 litre with deionised water. Mix well and take a 100 mls±1 ml aliquot using a 100 mls pipette immediately. Measure and record the pH and temperature of the sample using a pH meter capable of reading to ±0.01 pH units, with stirring, ensuring temperature is 21° C.+/−2° C. Titrate whilst stirring with 0.2M hydrochloric acid until pH measures exactly 7.5. Note the millilitres of hydrochloric acid used. Take the average titre of three identical repeats. Carry out the calculation described above to calculate RA to pH 7.5.

The RA will be greater than 4 and preferably greater than 6 and most preferably greater than 7.5 or even greater than 8 or 8.5 or higher.

It has been found that a robust alkalinity system is beneficial in the detergent compositions of the invention because it prevents malodours usually associated with the presence of lipase enzymes. Without wishing to be bound by theory the inventors work suggests that this is because the alkalinity in the wash neutralises the malodorous fatty acids produced by break-down of fatty soils by the lipase enzymes and then after neutralisation, calcium salts of the fatty acids form having a significantly lower vapour pressure than the protonated fatty acids released by the enzymes.

Adequate reserve alkalinity may be provided, for example, by one or more of alkali metal silicates (excluding crystalline layered silicate), typically amorphous silicate salts, generally 1.2 to 2.2 ratio sodium salts, alkali metal typically sodium carbonate, bicarbonate and/or sesquicarbonates. STPP and persalts such as perborates and percarbonates also contribute to alkalinity. Buffering is necessary to maintain an alkaline pH during the wash process counteracting the acidity of soils, especially fatty acids liberated by the lipase enzyme.

The detergent composition preferably comprises from 0 wt % to 50 wt % silicate salt, more usually 5 to 30 wt % silicate salt, or 7 to 20 wt % silicate salt, usually sodium silicate.

In order to provide the desired reserve alkalinity the detergent compositions of the invention may comprise a carbonate salt, typically from 1 wt % to 70 wt %, or from 5 wt % to 50 wt % or from 10 wt % to 30 wt % carbonate salt. Preferred carbonate salts are sodium carbonate and/or sodium bicarbonate and/or sodium sesquicarbonate. The carbonate salt may be incorporated into the detergent composition wholly or partially via a mixed salt such as Burkeite. A highly preferred carbonate salt is sodium carbonate. Preferably, the composition may comprise from 5 wt % to 50 wt % sodium carbonate, or from 10 to 40 wt % or even 15 to 35 wt % sodium carbonate. It may also be desired for the composition to comprise from 1 wt % to 20 wt % sodium bicarbonate, or even 2 to 10 or 8 wt %.

If zeolite is present, it may be desired for the weight ratio of sodium carbonate and/or sodium silicate to zeolite builder to be at least 5:1, preferably at least 10:1, or at least 15:1, or at least 20:1 or even at least 25:1

The carbonate salt, or at least part thereof, is typically in particulate form, typically having a weight average particle size in the range of from 200 to 500 micrometers. However, it may be preferred for the carbonate salt, or at least part thereof, to be in micronised particulate form, typically having a weight average particle size in the range of from 4 to 40 micrometers; this is especially preferred when the carbonate salt, or at least part thereof, is in the form of a co-particulate admixture with a detersive surfactant, such as an alkoxylated anionic detersive surfactant.

In order to provide the required reserve alkalinity, preferably the levels of carbonate and/or silicate salts, typically sodium carbonate and sodium silicate will be from 10 to 70 wt %, or from 10 or even 15 to 50 wt % based on the total weight of the composition.

Surfactant

A highly preferred adjunct component of the compositions of the invention is a surfactant. Preferably, the detergent composition comprises one or more surfactants. Typically, the detergent composition comprises (by weight of the composition) from 0% to 50%, preferably from 5% and more preferably from 10 or even 15 wt % to 40%, or to 30%, or to 20% one or more surfactants. Preferred surfactants are anionic surfactants, non-ionic surfactants, cationic surfactants, zwitterionic surfactants, amphoteric surfactants, cationic surfactants and mixtures thereof.

Anionic Surfactants

Suitable anionic surfactants typically comprise one or more moieties selected from the group consisting of carbonate, phosphate, phosphonate, sulphate, sulphonate, carboxylate and mixtures thereof. The anionic surfactant may be one or mixtures of more than one of $C_{8-18}$ alkyl sulphates and $C_{8-18}$ alkyl sulphonates. Suitable anionic surfactants incorporated alone or in mixtures in the compositions of the invention are also the $C_{8-18}$ alkyl sulphates and/or $C_{8-18}$ alkyl sulphonates optionally condensed with from 1 to 9 moles of $C_{1-4}$ alkylene oxide per mole of $C_{8-18}$ alkyl sulphate and/or $C_{8-18}$ alkyl sulphonate. The alkyl chain of the $C_{8-18}$ alkyl sulphates and/or $C_{8-18}$ alkyl sulphonates may be linear or branched, preferred branched alkyl chains comprise one or more branched moieties that are $C_{1-6}$ alkyl groups. More particularly, suitable anionic surfactants include the $C_{10}$-$C_{20}$ primary, branched-chain, linear-chain and random-chain alkyl sulphates (AS), typically having the following formula:

$$CH_3(CH_2)_xCH_2\text{—}OSO_3^-M^+$$

wherein, M is hydrogen or a cation which provides charge neutrality, preferred cations are sodium and ammonium cations, wherein x is an integer of at least 7, preferably at least 9; $C_{10}$-$C_{18}$ secondary (2,3) alkyl sulphates, typically having the following formulae:

$$CH_3(CH_2)_x\underset{}{\overset{\overset{\displaystyle OSO_3^-M^+}{|}}{(CH)}}CH_3 \quad \text{or} \quad CH_3(CH_2)_y\overset{\overset{\displaystyle OSO_3^-M^+}{|}}{(CH)}CH_2CH_3$$

wherein, M is hydrogen or a cation which provides charge neutrality, preferred cations include sodium and ammonium cations, wherein x is an integer of at least 7, preferably at least 9, y is an integer of at least 8, preferably at least 9; $C_{10}$-$C_{18}$ alkyl alkoxy carboxylates; mid-chain branched alkyl sulphates as described in more detail in U.S. Pat. Nos. 6,020,303 and 6,060,443; modified alkylbenzene sulphonate (MLAS) as described in more detail in WO 99/05243, WO 99/05242, WO 99/05244, WO 99/05082, WO 99/05084, WO 99/05241, WO 99/07656, WO 00/23549, WO 00/23548 and mixtures thereof.

Preferred anionic surfactants are $C_{8-18}$ alkyl benzene sulphates and/or $C_{8-18}$ alkyl benzene sulphonates. The alkyl chain of the $C_{8-18}$ alkyl benzene sulphates and/or $C_{8-18}$ alkyl benzene sulphonates may be linear or branched, preferred branched alkyl chains comprise one or more branched moieties that are $C_{1-6}$ alkyl groups.

Other preferred anionic surfactants are selected from the group consisting of: $C_{8-18}$ alkenyl sulphates, $C_{8-18}$ alkenyl sulphonates, $C_{8-18}$ alkenyl benzene sulphates, $C_{8-18}$ alkenyl benzene sulphonates, $C_{8-18}$ alkyl di-methyl benzene sulphate, $C_{8-18}$ alkyl di-methyl benzene sulphonate, fatty acid ester sulphonates, di-alkyl sulphosuccinates, and combinations thereof. Other useful anionic surfactants herein include the esters of alpha-sulfonated fatty acids, typically containing from 6 to 20 carbon atoms in the fatty acid group and from 1 to 10 carbon atoms in the ester group; 2-acyloxy-alkane-1-sulfonic acid and salts thereof, typically containing from about 2 to 9 carbon atoms in the acyl group and from about 9 to 23 carbon atoms in the alkane moiety; alpha-olefin sulfonates (AOS), typically containing from about 12 to 24 carbon atoms; and beta-alkoxy alkane sulfonates, typically containing from about 1 to 3 carbon atoms in the alkyl group and from about 8 to 20 carbon atoms in the alkane moiety. Also useful are the sulphonation products of fatty acid esters containing an alkyl group typically with from 10 to 20 carbon atoms. Preferred are $C_{1-4}$, most preferably methyl ester sulphonates. Preferred are $C_{16-18}$ methyl ester sulphonates (MES).

The anionic surfactants may be present in the salt form. For example, the anionic surfactant(s) may be an alkali metal salt of any of the above. Preferred alkali metals are sodium, potassium and mixtures thereof.

Preferred anionic detersive surfactants are selected from the group consisting of: linear or branched, substituted or unsubstituted, $C_{12-18}$ alkyl sulphates; linear or branched, substituted or unsubstituted, $C_{10-13}$ alkylbenzene sulphonates, preferably linear $C_{10-13}$ alkylbenzene sulphonates; and mixtures thereof. Highly preferred are linear $C_{10-13}$ alkylbenzene sulphonates. Highly preferred are linear $C_{10-13}$ alkylbenzene sulphonates that are obtainable, preferably obtained, by sulphonating commercially available linear alkyl benzenes (LAB); suitable LAB include low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®.

It may be preferred for the anionic detersive surfactant to be structurally modified in such a manner as to cause the anionic detersive surfactant to be more calcium tolerant and less likely to precipitate out of the wash liquor in the presence of free calcium ions. This structural modification could be the introduction of a methyl or ethyl moiety in the vicinity of the head group of the anionic detersive surfactant, as this can lead to a more calcium tolerant anionic detersive surfactant due to steric hindrance of the head group, which may reduce the affinity of the anionic detersive surfactant for complexing with free calcium cations in such a manner as to cause precipitation out of solution. Other structural modifications include the introduction of functional moieties, such as an amine moiety, in the alkyl chain of the anionic detersive surfactant; this can lead to a more calcium tolerant anionic detersive surfactant because the presence of a functional group in the alkyl chain of an anionic detersive surfactant may minimise the undesirable physicochemical property of the anionic detersive surfactant to form a smooth crystal structure in the presence of free calcium ions in the wash liquor. This may reduce the tendency of the anionic detersive surfactant to precipitate out of solution.

Alkoxylated Anionic Surfactants

The composition may comprise an alkoxylated anionic surfactant. Where present such a surfactant will generally be present in amounts from 0.1 wt % to 40 wt %, generally 0.1 to 10 wt % based on the detergent composition as a whole. It may be preferred for the composition to comprise from 3 wt % to 5 wt % alkoxylated anionic detersive surfactant, or it may be preferred for the composition to comprise from 1 wt % to 3 wt % alkoxylated anionic detersive surfactant.

Preferably, the alkoxylated anionic detersive surfactant is a linear or branched, substituted or unsubstituted $C_{12-18}$ alkyl alkoxylated sulphate having an average degree of alkoxylation of from 1 to 30, preferably from 1 to 10. Preferably, the alkoxylated anionic detersive surfactant is a linear or branched, substituted or unsubstituted $C_{12-18}$ alkyl ethoxylated sulphate having an average degree of ethoxylation of from 1 to 10. Most preferably, the alkoxylated anionic detersive surfactant is a linear unsubstituted $C_{12-18}$ alkyl ethoxylated sulphate having an average degree of ethoxylation of from 3 to 7.

The alkoxylated anionic detersive surfactant may also increase the non-alkoxylated anionic detersive surfactant activity by making the non-alkoxylated anionic detersive surfactant less likely to precipitate out of solution in the presence of free calcium cations. Preferably, the weight ratio of non-alkoxylated anionic detersive surfactant to alkoxylated anionic detersive surfactant is less than 5:1, or less than 3:1, or less than 1.7:1, or even less than 1.5:1. This ratio gives optimal whiteness maintenance performance combined with a good hardness tolerency profile and a good sudsing profile. However, it may be preferred that the weight ratio of non-alkoxylated anionic detersive surfactant to alkoxylated anionic detersive surfactant is greater than 5:1, or greater than 6:1, or greater than 7:1, or even greater than 10:1. This ratio gives optimal greasy soil cleaning performance combined with a good hardness tolerency profile, and a good sudsing profile. Suitable alkoxylated anionic detersive surfactants are: Texapan LEST™ by Cognis; Cosmacol AES™ by Sasol; BES151™ by Stephan; Empicol ESC70/U™; and mixtures thereof.

Non-ionic Detersive Surfactant

The compositions of the invention may comprise non-ionic surfactant. Where present it is generally present in amounts of from 0.5 wt % to 20, more typically 0.5 to 10 wt % based on the total weight of the composition. The composition may comprise from 1 wt % to 7 wt % or from 2 wt % to 4 wt % non-ionic detersive surfactant. The inclusion of non-ionic detersive surfactant in the composition helps to provide a good overall cleaning profile, especially when laundering at high temperatures such as 60° C. or higher.

The non-ionic detersive surfactant can be selected from the group consisting of: $C_{12}$-$C_{18}$ alkyl ethoxylates, such as, NEODOL® non-ionic surfactants from Shell; $C_6$-$C_{12}$ alkyl phenol alkoxylates wherein the alkoxylate units are ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA, as described in more detail in U.S. Pat. No. 6,150,322; $C_{14}$-$C_{22}$ mid-chain branched alkyl alkoxylates, $BAE_x$, wherein x=from 1 to 30, as described in more detail in U.S. Pat. Nos. 6,153,577, 6,020,303 and 6,093,856; alkylpolysaccharides as described in more detail in U.S. Pat. No. 4,565,647, specifically alkylpolyglycosides as described in more detail in U.S. Pat. Nos. 4,483,780 and 4,483,779; polyhydroxy fatty acid amides as described in more detail in U.S. Pat. No. 5,332,528, WO 92/06162, WO 93/19146, WO 93/19038, and WO 94/09099; ether capped poly(oxyalkylated) alcohol surfactants as described in more detail in U.S. Pat. No. 6,482,994 and WO 01/42408; and mixtures thereof.

The non-ionic detersive surfactant could be an alkyl polyglucoside and/or an alkyl alkoxylated alcohol. Preferably the non-ionic detersive surfactant is a linear or branched, substituted or unsubstituted $C_{8-18}$ alkyl ethoxylated alcohol having an average degree of ethoxylation of from 1 to 50, more preferably from 3 to 40. Non-ionic surfactants having a degree of ethoxylation from 3 to 9 may be especially useful either. Nonionic surfactants having an HLB value of from 13 to 25, such as $C_{8-18}$ alkyl ethoxylated alcohols having an average degree of ethoxylation from 15 to 50, or even from 20 to 50 may also be preferred non-ionic surfactants in the compositions of the invention. Examples of these latter non-ionic surfactants are Lutensol A030 and similar materials disclosed in WO04/041982. These may be beneficial as they have good lime soap dispersant properties.

The non-ionic detersive surfactant not only provides additional soil cleaning performance but may also increase the anionic detersive surfactant activity by making the anionic detersive surfactant less likely to precipitate out of solution in the presence of free calcium cations. Preferably, the weight ratio of non-alkoxylated anionic detersive surfactant to non-ionic detersive surfactant is in the range of less than 8:1, or less than 7:1, or less than 6:1 or less than 5:1, preferably from 1:1 to 5:1, or from 2:1 to 5:1, or even from 3:1 to 4:1.

Cationic Detersive Surfactant

In one aspect of the invention, the detergent compositions are free of cationic surfactant. However, the composition optionally may comprise from 0.1 wt % to 10 or 5 wt % cationic detersive surfactant. When present however, preferably the composition comprises from 0.5 wt % to 3 wt %, or from 1% to 3 wt %, or even from 1 wt % to 2 wt % cationic detersive surfactant. This is the optimal level of cationic detersive surfactant to provide good cleaning. Suitable cationic detersive surfactants are alkyl pyridinium compounds, alkyl quaternary ammonium compounds, alkyl quaternary phosphonium compounds, and alkyl ternary sulphonium compounds. The cationic detersive surfactant can be selected from the group consisting of: alkoxylate quaternary ammonium (AQA) surfactants as described in more detail in U.S. Pat. No. 6,136,769; dimethyl hydroxyethyl quaternary ammonium as described in more detail in U.S. Pat. No. 6,004,922; polyamine cationic surfactants as described in more detail in WO 98/35002, WO 98/35003, WO 98/35004, WO 98/35005, and WO 98/35006; cationic ester surfactants as described in more detail in U.S. Pat. Nos. 4,228,042, 4,239,660, 4,260,529 and 6,022,844; amino surfactants as described in more detail in U.S. Pat. No. 6,221,825 and WO 00/47708, specifically amido propyldimethyl amine; and mixtures thereof. Preferred cationic detersive surfactants are quaternary ammonium compounds having the general formula:

$$(R)(R^1)(R^2)(R^3)N^+X^-$$

wherein, R is a linear or branched, substituted or unsubstituted $C_{6-18}$ alkyl or alkenyl moiety, $R^1$ and $R^2$ are independently selected from methyl or ethyl moieties, $R^3$ is a hydroxyl, hydroxymethyl or a hydroxyethyl moiety, X is an anion which provides charge neutrality, preferred anions include halides (such as chloride), sulphate and sulphonate. Preferred cationic detersive surfactants are mono-$C_{6-18}$ alkyl mono-hydroxyethyl di-methyl quaternary ammonium chlorides. Highly preferred cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride. Cationic surfactants such as Praepagen HY (tradename Clariant) may be useful and may also be useful as a suds booster.

The cationic detersive surfactant provides additional greasy soil cleaning performance. However, the cationic detersive surfactant may increase the tendency of any non-alkoxylated anionic detersive surfactant to precipitate out of solution. Preferably, the cationic detersive surfactant and any non-alkoxylated anionic detersive surfactant are separated in the detergent composition of the invention, for example if cationic surfactant is present, preferably the cationic and any anionic surfactant, particularly non-alkoxylated anionic surfactant will be present in the composition in separate particles. This minimises any effect that any cationic detersive surfactant may have on the undesirable precipitation of the anionic detersive surfactant, and also ensures that upon contact with water, the resultant wash liquor is not cloudy. If cationic surfactant is present, preferably the weight ratio of non-alkoxylated anionic detersive surfactant to cationic detersive surfactant is in the range of from 5:1 to 25:1, more preferably from 5:1 to 20:1 or from 6:1 to 15:1, or from 7:1 to 10:1, or even from 8:1 to 9:1.

Typically, the detergent composition comprises from 1 to 50 wt % anionic surfactant, more typically from 2 to 40 wt %. Alkyl benzene sulphonates are preferred anionic surfactants.

Preferred compositions of the present invention comprise at least two different surfactants in combination comprising at least one selected from a first group, the first group comprising alkyl benzene sulphonate and MES surfactant; and at least one selected from a second group, the second group comprising alkoxylated anionic surfactant, MES and alkoxylated non-ionic surfactant and alpha olefin sulfonates (AOS). A particularly preferred combination comprises alkyl benzene sulphonate, preferably LAS in combination with MES. A further particularly preferred combination comprises alkyl benzene sulphonate, preferably LAS with an alkoxylated anionic surfactant, preferably $C_{8-18}$ alkyl alkoxylated sulphate having an average degree of alkoxylation of from 1 to 10. A third particularly preferred combination comprises alkyl benzene sulphonate, preferably LAS in combination with an alkoxylated non-ionic surfactant, preferably $C_{8-18}$ alkyl ethoxylated alcohol having a degree of alkoxylation of from 15 to 50, preferably from 20 to 40.

The weight ratio of the surfactant from the first group to the weight ratio of the surfactant from the second group is typically 1:5 to 100:1, preferably 1:2 to 100:1 or 1:1 to 50:1 or even to 20:1 or 10:1. The levels of the surfactants are as described above under the specific classes of surfactants. Presence of AE3S and/or MES in the system is preferred on account of their exceptional hardness-tolerance and ability to disperse lime soaps which are formed during the wash by lipase.

In a further embodiment, the surfactant in the detergent compositions of the invention comprises at least three surfactants, at least one from each of the first and second groups defined above and in addition a third surfactant, preferably also from the first or second groups defined above.

The detergent compositions of the invention may surprisingly contain relatively low levels of surfactant and yet still perform good cleaning, on account of the soil removal functionality delivered by the lipase, so that the overall level of surfactant may be below 12 wt %, or 10 wt % or 8 wt % based on total weight of the composition Polymeric Polycarboxylate It may be desired for the compositions of the invention to comprise at least 0.1 wt %, or at least 0.5 wt %, or at least 2 or 3 wt %, or even at least 5 wt % polymeric polycarboxylates up to levels of 30 wt % or 20 wt % or 10 wt %. Preferred polymeric polycarboxylates include: polyacrylates, preferably having a weight average molecular weight of from 1,000 Da to 20,000 Da; co-polymers of maleic acid and acrylic acid, preferably having a molar ratio of maleic acid monomers to acrylic acid monomers of from 1:1 to 1:10 and a weight average molecular weight of from 10,000 Da to 200,000 Da, or preferably having a molar ratio of maleic acid monomers to acrylic acid monomers of from 0.3:1 to 3:1 and a weight average molecular weight of from 1,000 Da to 50,000 Da. Suitable polycarboxylates are the Sokalan CP, PA and HP ranges (BASF) such as Sokalan CP5, PA40 and HP22, and the Alcosperse range of polymers (Alco) such as Alcosperse 725, 747, 408, 412 and 420.

Soil Dispersant

It may also be preferred for the composition to comprise a soil dispersant having the formula:

$$bis((C_2H_5O)(C_2H_4O)n)(CH_3)—N^+—C_xH_{2x}—N^+—(CH_3)\text{-}bis((C_2H_5O)(C_2H_4O)n)$$

wherein, n=from 20 to 30, and x=from 3 to 8. Other suitable soil dispersants are sulphonated or sulphated soil dispersants having the formula:

$$\text{sulphonated or sulphated } bis((C_2H_5O)(C_2H_4O)n)(CH_3)\text{-}N^+\text{-}C_xH_{2x}\text{-}N^+\text{-}(CH_3)\text{-}bis((C_2H_5O)(C_2H_4O)n)$$

wherein, n=from 20 to 30, and x=from 3 to 8. Preferably, the composition comprises at least 1 wt %, or at least 2 wt %, or at least 3 wt % soil dispersants.

In a preferred embodiment of the invention, the detergent composition also comprises a suds booster, typically in amounts from 0.01 to 10 wt %, preferably in amounts from 0.02 to 5 wt % based on the total weight of the composition. Suitable suds boosters include fatty acid amides, fatty acid alkalonamides, betaines, sulfobetaines and amine oxides. Particularly preferred materials are cocamidopropyl betaine, cocomonoethanolamide and amine oxide. A suitable amine oxide is Admox 12, supplied by Albemarle.

Lime Soap Dispersants

Since these lipase enzymes release soil into the wash water, it may be particularly preferred for the detergent compositions of the invention to additionally comprise anti-redeposition polymers such as the polymeric polycarboxylates described above. In addition, or alternatively, cellulose ethers such as carboxymethyl cellulose (CMC) will be useful. A suitable CMC is Tylose CR1500 G2, sold by Clariant. Suitable polymers are also sold by Andercol, Colombia under the Textilan brand name.

It is especially preferred to include additives with lime soap dispersancy functionality such as the aforementioned MES, AES, highly ethoxylated nonionic surfactant or polymers showing excellent lime soap dispersancy such as Acusol 460N (Rohm & Haas). Lists of suitable lime soap dispersants are given in the following references and documents cited therein.

WO9407974 (P&G), WO9407984 (P&G), WO9407985 (P&G), WO9504806 (P&G), WO9703379 (P&G), U.S. Pat. No. 6,770,610 (Clariant), EP0324568 (Rohm & Haas), EP0768370 (Rohm & Haas), M. K. Nagarajan and W. F. Masler, Cosmetics and Toiletries, 1989, 104, pp71-73, W. M. Linfield, Tenside Surf. Det, 1990, 27, pp 159-161, R. G. Bistline et al, J. Am. Oil Chem. Soc, 1972, 49, pp 63-69

Presence of a soil release polymer has been found to be especially beneficial in further strengthening the stain removal and cleaning benefits of the development, especially on synthetic fibres. Modified cellulose ethers such as methyl hydroxyethyl cellulose (MHEC), for example as sold by Clariant as Tylose MH50 G4 and Tylose MH300 G4, are preferred. Polyester-based Soil Release Polymers are especially preferred as they can also be effective as lime soap dispersants. Examples of suitable materials are Repel-o-Tex PF (supplied by Rhodia), Texcare SRA100 (supplied by Clariant) and Sokalan SR100 (BASF)

The formulations may contain one or more other enzymes in addition to the first wash lipase, for example protease, amylase, cellulase (especially endoglucanase), pectate lyase and/or mannanase.

The detergent compositions of the invention may be in any convenient form such as solids such as powdered or granular or tablet solids, bars, or liquids which may be aqueous or on-aqueous, gels or liquigels. Any of these forms may be partially or completely encapsulated. However, the present invention particularly relates to solid detergent compositions, especially granular compositions. Where the detergent compositions of the invention are solid, conventionally, surfactants are incorporated into agglomerates, extrudates or spray dried particles along with solid materials, usually builders, and these may be admixed to produce a fully formulated detergent composition according to the invention. When present in the granular form the detergent compositions of the present invention are preferably those having an overall bulk density of from 350 to 1200 g/l, more preferably 450 to 1000 g/l or even 500 to 900 g/. Preferably, the detergent particles of the detergent composition in a granular form have a size average particle size of from 200 μm to 2000 μm, preferably from 350 μm to 600 μm.

Generally the detergent compositions of the invention will comprise a mixture of detergent particles including combinations of agglomerates, spray-dried powders and/or dry added materials such as bleaching agents, enzymes etc.

In one aspect of the invention the detergent compositions of the invention comprise an anionic surfactant from the list above which is a non-alkoxylated anionic detersive surfactant and this is preferably incorporated into the detergent composition in particulate form, such as via an agglomerate, a spray-dried powder, an extrudate, a bead, a noodle, a needle or a flake. Spray-dried particles are preferred. If via an agglomerate, the agglomerate preferably comprises at least 20%, by weight of the agglomerate, of a non-alkoxylated anionic detersive surfactant, more preferably from 25 wt % to 65 wt %, by weight of the agglomerate, of a non-alkoxylated anionic detersive surfactant. It may be preferred for part of the non-alkoxylated anionic detersive surfactant to be in the form of a spray-dried powder (e.g. a blown powder), and for part of the non-alkoxylated anionic detersive surfactant to be in the form of a non-spray-dried powder (e.g. an agglomerate, or an extrudate, or a flake such as a linear alkyl benzene sulphonate flake; suitable linear alkyl benzene sulphonate flakes are supplied by Pilot Chemical under the tradename F90®, or by Stepan under the tradename Nacconol 90G®). This is especially preferred when it is desirable to incorporate high levels of non-alkoxylated anionic detersive surfactant in the composition.

Any alkoxylated anionic detersive surfactant may be incorporated into the detergent compositons of the invention via a spray-dried particle of a non-spray-dried powder such as an extrudate, agglomerate, preferably an agglomerate. Non-spray dried particles are preferred when it is desirable to incorporate high levels of alkoxylated anionic detersive surfactant in the composition Any non-ionic detersive surfactant, or at least part thereof, can be incorporated into the composition in the form of a liquid spray-on, wherein the non-ionic detersive surfactant, or at least part thereof, in liquid form (e.g. in the form of a hot-melt) is sprayed onto the remainder of the composition. The non-ionic detersive surfactant, or at least part thereof, may be in included into a particulate for incorporation into the detergent composition of the invention and the non-ionic detersive surfactant, or at least part thereof, may be dry-added to the remainder of the composition. The non-ionic surfactant, or at least part thereof, may be in the form of a co-particulate admixture with a solid carrier material such as carbonate salt, sulphate salt, burkeite, silica or any mixture thereof.

Any non-ionic detersive surfactant, or at least part thereof, may be in a co-particulate admixture with either an alkoxylated anionic detersive surfactant, a non-alkoxylated anionic detersive surfactant or a cationic detersive surfactant. The non-ionic detersive surfactant, or at least part thereof, may be agglomerated or extruded with either an alkoxylated anionic detersive surfactant, a non-alkoxylated anionic detersive surfactant or a cationic detersive surfactant.

The cationic detersive surfactant if present may be incorporated into the composition by incorporation in a particulate, such as a spray-dried powder, an agglomerate, an extrudate, a flake, a noodle, a needle, or any combination thereof. Preferably, the cationic detersive surfactant, or at least part thereof, is in the form of a spray-dried powder or an agglomerate.

First, Second and Third Surfactant Components

In a further aspect of the invention a detergent composition is provided comprising granular components, and comprising at least two separate surfactant components or even at least three separate surfactant components: a first, a second and an optional third surfactant component. These separate surfactant components may be present in separate particulates so that at least two surfactant components are separate from one another in the detergent composition.

The composition preferably comprises at least two separate surfactant components, each in particulate form. It may be preferred for the composition to comprise at least three separate surfactant components, each in particulate form.

The first surfactant component predominantly comprises an alkoxylated detersive surfactant. By predominantly comprises, it is meant that the first surfactant component comprises greater than 50%, by weight of the first surfactant component, of an alkoxylated anionic detersive surfactant, preferably greater than 60%, or greater than 70%, or greater than 80%, or greater than 90% or even essentially 100%, by weight of the first surfactant component, of an alkoxylated anionic detersive surfactant. Preferably, the first surfactant component comprises less than 10%, by weight of the first surfactant component, of a non-alkoxylated anionic detersive surfactant, preferably less than 5%, or less than 2%, or even 0%, by weight of the first surfactant component, of a non-alkoxylated anionic detersive surfactant. Preferably, the first surfactant component is essentially free from non-alkoxylated anionic detersive surfactant. By essentially free from non-alkoxylated anionic detersive surfactant it is typically meant that the first surfactant component comprises no deliberately added non-alkoxylated anionic detersive surfactant. This is especially preferred in order to ensure that the composition has good dispensing and dissolution profiles, and also to ensure that the composition provides a clear wash liquor upon dissolution in water.

If cationic detersive surfactant is present in the composition, then preferably the first surfactant component comprises less than 10%, by weight of the first surfactant component, of a cationic detersive surfactant, preferably less than 5%, or less than 2%, or even 0%, by weight of the first surfactant component, of a cationic detersive surfactant. Preferably, the first surfactant component is essentially free from cationic detersive surfactant. By essentially free from cationic detersive surfactant it is typically meant that the first surfactant component comprises no deliberately added cationic detersive surfactant. This is especially preferred in order to reduce the degree of surfactant gelling in the wash liquor.

The first surfactant component is preferably in the form of a spray-dried powder, an agglomerate, an extrudate or a flake. If the first surfactant component is in the form of an agglomerate particle or an extrudate particle, then preferably the particle comprises from 20% to 65%, by weight of the particle, of an alkoxylated anionic detersive surfactant. If the first surfactant component is in spray-dried particle form, then preferably the particle comprises from 10 wt % to 30 wt %, by weight of the particle, of an alkoxylated anionic detersive surfactant. The first surfactant component may be in the form of a co-particulate admixture with a solid carrier material. The solid carrier material can be a sulphate salt and/or a carbonate salt, preferably sodium sulphate and/or sodium carbonate.

The second surfactant component predominantly comprises a non-alkoxylated detersive surfactant. By predominantly comprises, it is meant the second surfactant component comprises greater than 50%, by weight of the second surfactant component, of a non-alkoxylated anionic detersive surfactant, preferably greater than 60%, or greater than 70%, or greater than 80%, or greater than 90% or even essentially 100%, by weight of the second surfactant component, of a non-alkoxylated anionic detersive surfactant. Preferably, the second surfactant component comprises less than 10%, by weight of the second surfactant component, of an alkoxylated anionic detersive surfactant, preferably less than 5%, or less than 2%, or even 0%, by weight of the second surfactant component, of an alkoxylated anionic detersive surfactant. If cationic detersive surfactant is present in the composition, then preferably the second surfactant component comprises less than 10%, by weight of the second surfactant component, of a cationic detersive surfactant, preferably less than 5%, or less than 2%, or even 0%, by weight of the second surfactant component, of a cationic detersive surfactant. Preferably, the second surfactant component is essentially free from alkoxylated anionic detersive surfactant. By essentially free from alkoxylated anionic detersive surfactant it is typically meant that the second surfactant component comprises no deliberately added alkoxylated anionic detersive surfactant. Preferably, the second surfactant component is essentially free from cationic detersive surfactant. By essentially free from cationic detersive surfactant it is typically meant that the second surfactant component comprises no deliberately added cationic detersive surfactant. This is especially preferred in order to ensure that the composition has good dispensing and dissolution profiles, and also to ensure that the composition provides a clear wash liquor upon dissolution in water.

The second surfactant component may be in the form of a spray-dried powder, a flash-dried powder, an agglomerate or an extrudate. If the second surfactant component is in the form of an agglomerate particle, then preferably the particle from 5% to 50%, by weight of the particle, of a non-alkoxylated anionic detersive surfactant, or from 5 wt % to 25 wt % non-alkoxylated anionic detersive surfactant. The second surfactant component may be in form of a co-particulate admixture with a solid carrier material. The solid carrier material can be a sulphate salt and/or a carbonate salt, preferably sodium sulphate and/or sodium carbonate.

Although the detergent compositions of the invention may be substantially free of cationic surfactant, if present, the cationic surfactant may be present in a third surfactant component or may be incorporated into a spray-dried particle with at least some anionic surfactant. If present in a third component, it may be beneficial to have the third surfactant component predominantly comprising a cationic detersive surfactant. By predominantly comprises, it is meant the third surfactant component comprises greater than 50%, by weight of the third surfactant component, of a cationic detersive surfactant, preferably greater than 60%, or greater than 70%, or greater than 80%, or greater than 90% or even essentially 100%, by weight of the third surfactant component, of a cationic detersive surfactant. Preferably, the third surfactant component comprises less than 10%, by weight of the third surfactant component, of an alkoxylated anionic detersive surfactant, preferably less than 5%, or less than 2%, or even essentially 0%, by weight of the third surfactant component, of an alkoxylated anionic detersive surfactant. Preferably the third surfactant component comprises less than 10%, by weight of the third surfactant component, of a non-alkoxylated anionic detersive surfactant, preferably less than 5%, or less than 2%, or even 0%, by weight of the third surfactant component, of a non-alkoxylated anionic detersive surfactant. Preferably, the third surfactant component is essentially free from alkoxylated anionic detersive surfactant. By essentially free from alkoxylated anionic detersive surfactant it is typically meant that the third surfactant component comprises no deliberately added alkoxylated anionic detersive surfactant. Preferably, the third surfactant component is essentially free from non-alkoxylated anionic detersive surfactant. By essentially free from non-alkoxylated anionic detersive surfactant it is typically meant that the third surfactant component comprises no deliberately added non-alkoxylated anionic detersive surfactant. This is especially preferred in order to ensure that the composition has good dispensing and dissolution profiles, and also to ensure that the composition provides a clear wash liquor upon dissolution in water.

The third surfactant component is preferably in the form of a spray-dried powder, a flash-dried powder, an agglomerate or an extrudate. If the third surfactant component is in the form of an agglomerate particle, then preferably the particle comprises from 5% to 50%, by weight of the particle, of cationic detersive surfactant, or from 5 wt % to 25 wt % cationic detersive surfactant. The third surfactant component may be in form of a co-particulate admixture with a solid carrier material. The solid carrier material can be a sulphate salt and/or a carbonate salt, preferably sodium sulphate and/or sodium carbonate. Optional Detersive Adjuncts Optionally, the detergent ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. and in Great Britain Patent Application No. 9705617.0, Trinh et al., published Sep. 24, 1997. Such adjuncts are included in detergent compositions at their conventional art-established levels of use, generally from 0 wt % to about 80 wt % of the detergent ingredients, preferably from about 0.5 wt % to about 20 wt % and can include color speckles, suds boosters, suds suppressors, antitarnish and/or anticorrosion agents, soil-suspending agents, soil release agents, dyes, fillers, optical brighteners, germicides, alkalinity sources, hydrotropes, antioxidants, enzymes, enzyme stabilizing agents, solvents, solubilizing agents, chelating agents, clay soil removal/anti-redeposition agents, polymeric dispersing agents, processing aids, fabric softening components, static control agents, bleaching agents, bleaching activators, bleach stabilizers, dye-transfer inhibitors, flocculants, fabric softeners, suds supressors, fabric integrity agents, perfumes, whitening agents, photobleach, alkali metal sulphate salts, sulphamic acid, sodium sulphate and sulphamic acid complexes, etc and combinations thereof. The precise nature of these additional components, and levels of incorporation thereof will depend on the physical form of the composition or component, and the precise nature of the washing operation for which it is to be used.

Preferred zwitterionic surfactants comprise one or more quaternized nitrogen atoms and one or more moieties selected from the group consisting of: carbonate, phosphate, sulphate, sulphonate, and combinations thereof. Preferred zwitterionic surfactants are alkyl betaines. Other preferred zwitterionic surfactants are alkyl amine oxides. Catanionic surfactants which are complexes comprising a cationic surfactant and an anionic surfactant may also be included. Typically, the molar ratio of the cationic surfactant to anionic surfactant in the complex is greater than 1:1, so that the complex has a net positive charge.

A preferred adjunct component is a bleaching agent. Preferably, the detergent composition comprises one or more bleaching agents. Typically, the composition comprises (by weight of the composition) from 1% to 50% of one or more bleaching agent. Preferred bleaching agents are selected from the group consisting of sources of peroxide, sources of peracid, bleach boosters, bleach catalysts, photo-bleaches, and combinations thereof. Preferred sources of peroxide are selected from the group consisting of: perborate monohydrate, perborate tetra-hydrate, percarbonate, salts thereof, and combinations thereof. Preferred sources of peracid are selected from the group consisting of: bleach activator typically with a peroxide source such as perborate or percarbonate, preformed peracids, and combinations thereof. Preferred bleach activators are selected from the group consisting of: oxy-benzene-sulphonate bleach activators, lactam bleach activators, imide bleach activators, and combinations thereof. A preferred source of peracid is tetra-acetyl ethylene diamine (TAED)and peroxide source such as percarbonate. Preferred oxy-benzene-sulphonate bleach activators are selected from the group consisting of: nonanoyl-oxy-benzene-sulponate, 6-nonamido-caproyl-oxy-benzene-sulphonate, salts thereof, and combinations thereof. Preferred lactam bleach activators are acyl-caprolactams and/or acyl-valerolactams. A preferred imide bleach activator is N-nonanoyl-N-methyl-acetamide.

Preferred preformed peracids are selected from the group consisting of N,N-pthaloyl-amino-peroxycaproic acid, nonyl-amido-peroxyadipic acid, salts thereof, and combinations thereof. Preferably, the STW-composition comprises one or more sources of peroxide and one or more sources of peracid. Preferred bleach catalysts comprise one or more transition metal ions. Other preferred bleaching agents are di-acyl peroxides. Preferred bleach boosters are selected from the group consisting of: zwitterionic imines, anionic imine polyions, quaternary oxaziridinium salts, and combinations thereof. Highly preferred bleach boosters are selected from the group consisting of: aryliminium zwitterions, aryliminium polyions, and combinations thereof. Suitable bleach boosters are described in U.S. Pat. Nos. 360,568, 5,360,569 and 5,370,826.

A preferred adjunct component is an anti-redeposition agent. Preferably, the detergent composition comprises one or more anti-redeposition agents. Preferred anti-redeposition agents are cellulosic polymeric components, most preferably carboxymethyl celluloses.

A preferred adjunct component is a chelant. Preferably, the detergent composition comprises one or more chelants. Preferably, the detergent composition comprises (by weight of the composition) from 0.01% to 10% chelant, or 0.01 to 5 wt % or 4 wt % or 2 wt %. Preferred chelants are selected from the group consisting of: hydroxyethane-dimethylene-phosphonic acid, ethylene diamine tetra(methylene phosphonic) acid, diethylene triamine pentacetate, ethylene diamine tetraacetate, diethylene triamine penta(methyl phosphonic) acid, ethylene diamine disuccinic acid, and combinations thereof.

A preferred adjunct component is a dye transfer inhibitor. Preferably, the detergent composition comprises one or more dye transfer inhibitors. Typically, dye transfer inhibitors are polymeric components that trap dye molecules and retain the dye molecules by suspending them in the wash liquor. Preferred dye transfer inhibitors are selected from the group consisting of: polyvinylpyrrolidones, polyvinylpyridine N-oxides, polyvinylpyrrolidone-polyvinylimidazole copolymers, and combinations thereof.

Preferred adjunct components include other enzymes. Preferably, the detergent composition comprises one or more additional enzymes. Preferred enzymes are selected from then group consisting of: amylases, arabinosidases, carbohydrases, cellulases, chondroitinases, cutinases, dextranases, esterases, B-glucanases, gluco-amylases, hyaluronidases, keratanases, laccases, ligninases, lipoxygenases, malanases, mannanases, oxidases, pectinases, pentosanases, peroxidases, phenoloxidases, phospholipases, proteases, pullulanases, reductases, tannases, transferases, xylanases, xyloglucanases, and combinations thereof. Preferred additional enzymes are selected from the group consisting of: amylases, carbohydrases, cellulases, proteases, and combinations thereof.

A preferred adjunct component is a fabric integrity agent. Preferably, the detergent composition comprises one or more fabric integrity agents. Typically, fabric integrity agents are polymeric components that deposit on the fabric surface and prevent fabric damage during the laundering process. Preferred fabric integrity agents are hydrophobically modified celluloses. These hydrophobically modified celluloses reduce fabric abrasion, enhance fibre-fibre interactions and reduce dye loss from the fabric. A preferred hydrophobically modified cellulose is described in WO99/14245. Other preferred fabric integrity agents are polymeric components and/or oligomeric components that are obtainable, preferably obtained, by a process comprising the step of condensing imidazole and epichlorhydrin.

A preferred adjunct component is a salt. Preferably, the detergent composition comprises one or more salts. The salts can act as alkalinity agents, buffers, builders, co-builders, encrustation inhibitors, fillers, pH regulators, stability agents, and combinations thereof. Typically, the detergent composition comprises (by weight of the composition) from 5% to 60% salt. Preferred salts are alkali metal salts of aluminate, carbonate, chloride, bicarbonate, nitrate, phosphate, silicate, sulphate, and combinations thereof. Other preferred salts are alkaline earth metal salts of aluminate, carbonate, chloride, bicarbonate, nitrate, phosphate, silicate, sulphate, and combinations thereof. Especially preferred salts are sodium sulphate, sodium carbonate, sodium bicarbonate, sodium silicate, sodium sulphate, and combinations thereof. Optionally, the alkali metal salts and/or alkaline earth metal salts may be anhydrous.

A preferred adjunct component is a soil release agent. Preferably, the detergent composition comprises one or more soil release agents. Typically, soil release agents are polymeric compounds that modify the fabric surface and prevent the redeposition of soil on the fabric. Preferred soil release agents are copolymers, preferably block copolymers, comprising one or more terephthalate unit. Preferred soil release agents are copolymers that are synthesised from dimethylterephthalate, 1,2-propyl glycol and methyl capped polyethyleneglycol. Other preferred soil release agents are anionically end capped polyesters.

Softening System

The detergent compositions of the invention may comprise softening agents for softening through the wash such as clay optionally also with flocculent and enzymes.

Further more specific description of suitable detergent components can be found in WO97/11151.

Washing Method

The invention also includes methods of washing textiles comprising contacting textiles with an aqueous solution comprising the detergent composition of the invention.

The invention may be particularly beneficial at low water temperatures such as below 30° C. or below 25 or 20° C. Typically the aqueous wash liquor will comprise at least 100 ppm, or at least 500 ppm of the detergent composition

EXAMPLES

The following are examples of the invention.

| Ingredient | A | B | C | D | E | F | G |
|---|---|---|---|---|---|---|---|
| Sodium linear $C_{11-13}$ alkylbenzene sulfonate | 19 | 14.5 | 10 | 14 | 5 | 6 | 20 |
| $R_2N^+(CH_3)_2(C_2H_4OH)$, wherein $R_2 = C_{12-14}$ alkyl group | Nil | 0.5 | Nil | 0.2 | Nil | Nil | Nil |
| $R_2N^+(CH_3)_2(C_2H_4OH)$, wherein $R_2 = C_{8-10}$ alkyl group | 0.55 | Nil | Nil | Nil | 0.6 | 0.9 | Nil |
| Sodium $C_{12}$-$C_{15}$ alcohol ether sulfate containing an average of 3 moles of ethylene oxide | 1.0 | 1.0 | 0.5 | Nil | 3.6 | Nil | 1.5 |
| Sodium $C_{16-18}$ methyl ester sulphonate (MES) | Nil | 3.0 | 2.0 | Nil | Nil | 3.0 | Nil |
| $C_{12-18}$ linear alcohol ethoxylate condensed with an average of 3-9 moles of ethylene oxide per mole of alkyl alcohol | Nil | Nil | Nil | Nil | Nil | 9.2 | 1.1 |
| $C_{13-15}$ alcohol ethoxylate condensed with an average of 30 moles of ethylene oxide per mole of alkyl alcohol (Lutensol AO30 from BASF) | Nil | Nil | Nil | Nil | Nil | Nil | 3.9 |
| Citric acid | Nil | Nil | Nil | 1.0 | 3.2 | 2.6 | Nil |
| Sodium tripolyphosphate (anhydrous weight given) | 9.0 | 3.0 | Nil | 6.6 | Nil | Nil | 8.0 |
| Zeolite A | Nil | 4.4 | Nil | 2.0 | 0.5 | Nil | Nil |
| Sodium carboxymethyl cellulose | 0.6 | 0.5 | 0.3 | 0.3 | 0.2 | 0.7 | 0.3 |
| Sodium polyacrylate polymer having a weight average molecular weight of from 3000 to 5000 | 1.0 | 1.0 | Nil | 2.6 | Nil | Nil | 1.8 |
| Copol of maleic/acrylic acid, having wt average molecular wt of from 50,000 to 90,000, and ratio of maleic to acrylic acid is from 1:3 to 1:4 (Sokalan CP5 from BASF) | Nil | Nil | 1.0 | Nil | 10.9 | 12.0 | Nil |

-continued

| Ingredient | A | B | C | D | E | F | G |
|---|---|---|---|---|---|---|---|
| Lime soap dispersing polycarboxylate (Acusol 460N from Rohm & Haas) | Nil | Nil | 0.4 | Nil | Nil | Nil | 0.2 |
| Diethylene triamine pentaacetic acid | 0.3 | 0.3 | 0.2 | 0.3 | Nil | Nil | 0.2 |
| Ethylene diamine disuccinic acid | Nil | Nil | Nil | Nil | 0.3 | 0.2 | Nil |
| Proteolytic enzyme having an enzyme activity of from 15 mg/g to 70 mg/g | 0.2 | 0.2 | 0.2 | 0.7 | 0.3 | 0.3 | 0.2 |
| Amyolytic enzyme having an enzyme activity of from 25 mg/g to 50 mg/g | 0.1 | 0.1 | 0.1 | 0.4 | 0.2 | 0.4 | Nil |
| Lipex ® enzyme from Novozymes having an enzyme activity of 5 mg/g to 25 mg/g | 0.15 | 0.10 | 0.10 | 0.6 | 0.2 | 0.12 | 0.15 |
| Anhydrous sodium perborate monohydrate | 4.4 | Nil | Nil | 1.55 | Nil | Nil | Nil |
| Sodium percarbonate | Nil | Nil | Nil | Nil | 12.0 | 10.0 | 7.2 |
| Magnesium sulfate | 0.5 | Nil | Nil | 0.3 | 0.3 | 0.4 | 0.3 |
| Nonanoyl oxybenzene sulfonate | 1.0 | Nil | Nil | Nil | Nil | Nil | Nil |
| Tetraacetylethylenediamine | 0.28 | Nil | Nil | 0.28 | 3.2 | 2.9 | 3.0 |
| Brightener | 0.16 | 0.30 | 0.30 | 0.2 | 0.3 | 0.5 | 0.3 |
| Sodium carbonate | 20.0 | 17.0 | 17.0 | 22.0 | 17.0 | 20.0 | 10.0 |
| Sodium silicate (2.0 R) | 12.0 | 12.0 | 16.2 | 12.6 | 15.0 | 12.0 | 10.0 |
| Photobleach | 0.0035 | 0.0035 | 0.0035 | Nil | 0.0014 | 0.0012 | 0.0034 |
| Perfume spray-on | 0.2 | 0.2 | 0.2 | 0.12 | 0.34 | 0.37 | 0.1 |
| Starch encapsulated perfume | 0.2 | 0.2 | 0.2 | 0.1 | 0.1 | 0.2 | Nil |
| Suds suppressor granule | 0.3 | 0.2 | Nil | Nil | 0.3 | 0.4 | Nil |
| Soap | Nil | Nil | Nil | 2.1 | Nil | 1.0 | Nil |
| Na2SO4, misc and moisture | To 100% | To 100% | To 100% | To 100% | To 100% | To 100% | To 100% |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A detergent composition comprising from 0 to 8 wt % aluminosilicate (anhydrous basis) and/or phosphate builder wherein the total amount of phosphate and aluminosilicate does not exceed 8 wt %, said composition comprising from 10 wt % to 70 wt % carbonate salts, silicate salts, or mixtures thereof, said composition having a reserve alkalinity of greater than 4, and said composition comprising a lipase which is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15 Åof E1 or Q249 with a positively charged amino acid, at any of positions 1-11, 90, 95, 169, 171-175, 192-211, 213-226, 228-258, 260-262; and (c) comprises a peptide addition at the C-terminal; wherein said detergent composition is in solid form.

2. A detergent composition according to claim 1 comprising from 0 to less than 5 wt % aluminosilicate (anhydrous basis) and/or phosphate.

3. A detergent composition according to claim 1 having a reserve alkalinity greater than 7.5.

4. A detergent composition according to claim 1 additionally comprising from 0.1 to 40 wt % alkoxylated alkyl sulphate surfactant and/or from 0.1 to 40 wt % $C_{1-4}$ alkyl ester sulphonate.

5. A detergent composition according to claim 1 comprising from 0.1 to 40 wt % methyl ester sulphonate (MES).

6. A detergent composition according to claim 1 additionally comprising a suds booster in an amount from 0.05 to 2 wt %.

7. A detergent composition according to claim 6 in which the suds booster is selected from the group consisting of fatty acid amides, fatty acid alkanolamides, betaines, sulfobetaines, amine oxides and mixtures thereof.

8. A detergent composition according to claim 1 additionally comprising from 0.05 to 5 wt % soil release polymer.

9. A detergent composition according to claim 8 wherein the soil release polymer is selected from modified cellulose ethers such as methyl hydroxyethyl cellulose (MHEC) or polyester-based soil release polymers and mixtures thereof.

10. A detergent composition according to claim 1, wherein the lipase comprises a substitution selected from the group consisting of; S3R, S224R, P229R, T231R, N233R, D234R, T244R, and combinations thereof.

11. A detergent composition according to claim 1, wherein the lipase comprises a substitution selected from the group consisting of; T231R, N233R, and combinations thereof.

12. A detergent composition according to claim 1 which is in the form of granules.

13. A detergent composition comprising from 0 to 8 wt % aluminosilicate (anhydrous basis) and/or phosphate builder wherein the total amount of phosphate and aluminosilicate does not exceed 8 wt %, said composition comprising from 10 wt % to 70wt % carbonate salts, silicate salts, or mixtures thereof, said composition having a reserve alkalinity of greater than 4, and said composition comprising a lipase which is a polypeptide having an amino acid sequence which has at least 90% identity with the wild-type lipase derived from Humicola lanuginosa strain DSM 4109 and, compared to said wild-type lipase, comprises a substitution selected from the group consisting of S3R, S224R, P229R, T231R, N233R, D234R, T244R, and combinations thereof, wherein said detergent composition is in solid form.

14. A detergent composition according to claim 1, wherein the carbonate salts, silicate salts, or mixtures thereof are selected from the group consisting of sodium carbonate, sodium bicarbonate, sodium sesquicarbonate, sodium silicate, and mixtures thereof.

15. A detergent composition according to claim 1, wherein the carbonate salts, silicate salts, or mixture thereof are sodium carbonate and/or sodium silicate, and wherein when aluminosilicate builder is present, the weight ratio of sodium carbonate and/or sodium silicate to aluminosilicate builder is at least 5:1.

16. A detergent composition according to claim 1, wherein said composition comprises from 0.5 wt % to 8 wt % aluminosilicate (anhydrous basis) and/or phosphate builder.

17. A detergent composition according to claim 1, wherein said composition is essentially free from aluminosilicate builder and essentially free from phosphate builder.

18. A detergent composition according to claim 1, wherein the amino acid sequence further comprises a peptide addition at the N-terminal.

19. A detergent composition according to claim 18, wherein the amino acid sequence further comprises:

i) a negative amino acid in position E210 of said wild-type lipase;

ii) a negatively charged amino acid in the region corresponding to positions 90-101 of said wild-type lipase; and iii) a neutral or negative amino acid at a position corresponding to N94 of said wild-type lipase and/or has a negative or neutral net electric charge in the region corresponding to positions 90-101 of said wild-type lipase.

20. A detergent composition according to claim 1, wherein the amino acid sequence further comprises:

i) a negative amino acid in position E210 of said wild-type lipase;

ii) a negatively charged amino acid in the region corresponding to positions 90-101 of said wild-type lipase; and iii) a neutral or negative amino acid at a position corresponding to N94 of said wild-type lipase and/or has a negative or neutral net electric charge in the region corresponding to positions 90-101 of said wild-type lipase.

* * * * *